United States Patent
Gordon

(10) Patent No.: US 6,575,972 B1
(45) Date of Patent: Jun. 10, 2003

(54) WRAP SPRING CLAMP

(75) Inventor: Jeffrey D. Gordon, Vancover (CA)

(73) Assignee: Vanderbilt University, Nashville, TN (US)

( * ) Notice: Subject to any disclaimer, the term of this patent is extended or adjusted under 35 U.S.C. 154(b) by 141 days.

(21) Appl. No.: 09/843,627

(22) Filed: Apr. 27, 2001

Related U.S. Application Data

(60) Provisional application No. 60/200,251, filed on Apr. 28, 2000.

(51) Int. Cl.[7] ............................................... A61B 17/56
(52) U.S. Cl. ......................................................... 606/54
(58) Field of Search ............................. 606/54, 61, 72, 606/151, 59, 157; 403/229, 9, 111, 166, 325, 326, 327

(56) References Cited

U.S. PATENT DOCUMENTS

| | | | |
|---|---|---|---|
| 3,230,595 A | * | 1/1966 | Kedem ........................ 403/376 |
| 4,006,874 A | | 2/1977 | McGee |
| 4,170,995 A | | 10/1979 | Levine et al. |
| 4,724,883 A | | 2/1988 | Liebowitz |
| 5,217,438 A | * | 6/1993 | Davis et al. ................. 604/198 |
| 5,291,646 A | | 3/1994 | French |
| 5,381,989 A | | 1/1995 | Jackson |
| 5,551,660 A | | 9/1996 | Leduchowski |
| 5,553,822 A | * | 9/1996 | Barnard et al. ............. 248/302 |
| 5,674,221 A | | 10/1997 | Hein et al. |
| 5,704,098 A | | 1/1998 | Calmettes |
| 5,833,191 A | | 11/1998 | Gennep |
| 6,080,153 A | * | 6/2000 | Mata et al. ................... 606/54 |
| 6,355,039 B1 | * | 3/2002 | Troussel et al. ............... 606/61 |

* cited by examiner

*Primary Examiner*—David O. Reip
*Assistant Examiner*—D. Jacob Davis
(74) *Attorney, Agent, or Firm*—Stites & Harbison, PLLC; Richard S. Myers, Jr.

(57) ABSTRACT

A clamp with helical coils or springs defining a cavity to receive and secure rod members. The clamp also comprises a connection and tightening device for constricting the first and second helical coils around the respective rod members. These clamps have multiple uses including use as a device for securing a bone. In such a case, this embodiment may comprise a first and second stabilization bar, a pin, a pin attachment device, and a clamp. In another embodiment of the present invention, a clamp comprises connectors with cavities to house the helical springs. The connection and tightening device secures and tightens the first and second connectors by causing the helical springs to constrict about the rod member.

39 Claims, 10 Drawing Sheets

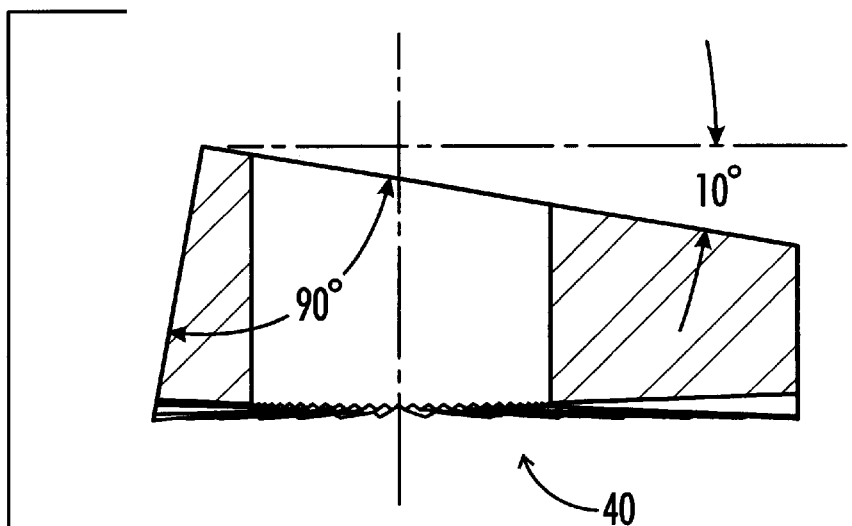
FIG. 8B
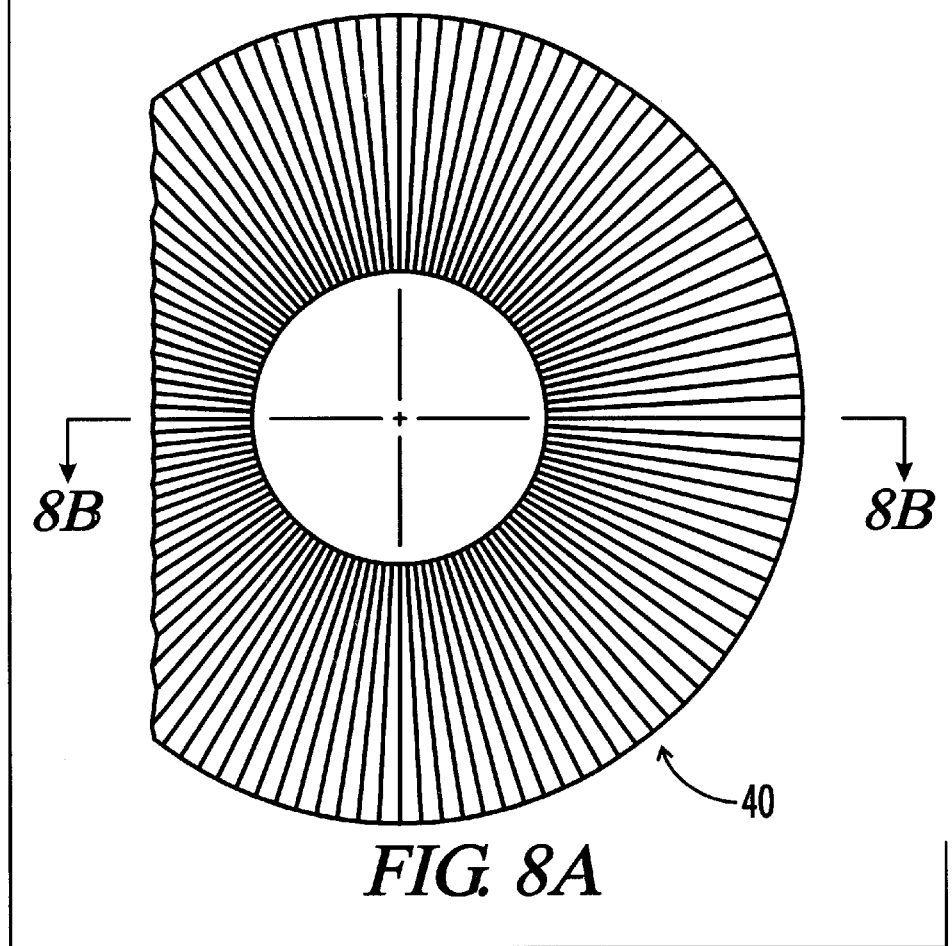
FIG. 8A
FIG. 8

WRAP SPRING CLAMP

The present invention claims priority to US Provisional Application No. 60/200,251 filed on Apr. 28, 2000.

FIELD OF THE INVENTION

The present invention relates to a clamp for connecting elongated parts such as rods, pins, pipes or the like. The parts may be cylindrical, and may be parallel or have any angular configuration.

BACKGROUND OF THE INVENTION

Several clamps for connecting and securing elongated parts and the like have been proposed. However, the clamps of the present invention is superior to other designs in part because the clamps of the present invention grip relatively large areas of the parts to be connected. Many other clamps have only small areas or lines of contact. Gripping a larger area derives at least two advantages. First, the clamping force is more effective. Second, the clamping force is better distributed and therefore less likely to mar or damage the clamped parts. Examples of prior art clamps include U.S. Pat. No. 5,551,660 to Leduchowski. This patent discloses a drum stick holder assembly having an adjustable fastener with a coupling to allow for clockwise or counterclockwise adjustment. Another coupling allows for forwards and backwards rotational adjustments. The assembly has one or two cylinders to house drum sticks. This patent fails to disclose or suggest the use of helical springs or coils that are present in the present invention.

U.S. Pat. No. 4,006,874 to McGee discloses a tube clamp device that includes a sleeve like assembly that has two identical semi-cylindrically shaped half sleeve members. The half sleeve members are sized to the tube diameter being clamped. This claim does not include any helical springs or coils and is designed to connect a tube to a fixed support such as a wall.

U.S. Pat. No. 4,170,995 to Levine, et al., discloses a holder for clamping in place a catheter or other hollow tube using a one piece jaw member mounted on a post with a nut threaded onto the post for adjusting the grip of the clamp. This clamp does not contain any helical springs or coils.

U.S. Pat. No. 5,291,646 to French discloses a clamp used to attach objects to a steering wheel or other type device. The clamp preferably is metal bent to the shape of a "U" or a "V". The "U" or "V" operate as jaws. This clamp has only lines or points of contact with its clamped part.

U.S. Pat. No. 5,774,098 to Calmettes discloses a clamping collar which uses a helical spring that provides pressure to the jaws of the clamp. In this patent, the helical spring or coil does not contact the rod onto which the collar is clamped. In this application, the spring is used to spread apart arms of a pair of pliers.

U.S. Pat. No. 5,833,191 to Gennep discloses a connector that includes a pair of jaws having concave facing gripping services. The connector is a holder for various different objects. The holder cooperates with a "vise-grip" type gripping device. The position at which a pair of jaws lock relative to one another is adjustable.

U.S. Pat. No. 5,381,989 to Jackson discloses an adjustable clamp using a helical spring that provides pressure on the jaws and lever arms of the clamp. Again, the helical spring used in this patent is not utilized in the same manner as the present invention.

U.S. Pat. No. 5,674,221 discloses an external fixator for the stabilization of a bone fracture using a "U" shaped clamp to secure the pin to the stabilization bar. The clamp holds the pin to the rod by forcing together two skewed cylinders. There are no helical springs included in the design of this clamp. This clamp grips with only lines or points of contact with its clamped part.

SUMMARY OF THE INVENTION

One of the novel features of the wrap spring clamp of the present invention is its method of gripping the elongated parts, including cylindrical parts. The clamp grips the parts by twisting a helical coil spring around each part. When the helical spring is twisted in the same direction as its coil, the diameter of the spring is reduced, thereby constricting a part placed within its bore.

Regarding the springs, machined springs, square wire springs, or round wire springs may be used. A machined spring or a square wire spring, when it is tightly wound, grips with nearly its entire inner surface area (the circumference of the bore multiplied by the working length of the spring). A round wire spring will grip along a line that follows the helix of the spring. Therefore, a machined or square wire spring will grip over a greater area than will a round wire spring.

In one embodiment of the present invention, the clamp resembles hinges and within each hinge is a helical spring. Either between the hinges and springs, or incorporated within the hinges or springs themselves, may be coupling devices such as toothed washers. The washers, when used, positively lock the angular configuration between the hinge components. A connection and tightening device such as a bolt passes through the clamp and permits a tightening operation to completely secure the connection. A preferable bolt is a single sex bolt that would require no tools to assemble or tighten. Optionally, the bolt may be made tamper resistant. Therefore, if used as a medical device for holding pins in a bone, the wearer would not be able to unfasten the clamp.

The composition of the clamp is not known to be critical and may be made from different materials depending upon the particular use. For example, the is clamp of the present invention may be fabricated of metal such as stainless steel, titanium, or aluminum. Additionally, the clamp of the present invention may be cast from a polymer or composite.

Because the improved clamp of the present invention secures rod-shaped parts, especially cylindrical or rod-shaped parts, in a new and improved manner, its commercial applications are potentially very broad and not limited to medical devices. This clamp could be incorporated into automobiles, aerospace structures and vehicles, sporting goods, agricultural machinery structures, appliances, furniture, and the like. In addition to orthopedic external fracture fixation, additional examples of uses of the clamp of the present invention include scaffolding and trusses, space structures, air frames, plumbing and chemical processing pipes, adjustable furniture such as computer monitor stands, and temporary fencing, to name a few.

Regarding examples of orthopedic functions, the wrap spring clamp of the present invention may be used as an external fixator clamp for rod to rod and rod to pin connections. Optionally, the clamp of the present invention requires no tools to assemble or to tighten. Therefore, a single tightening operation could secure the connection. Also, as mentioned above, the clamp may be made tamper resistant.

In one embodiment of the present invention, a clamp is disclosed for holding rod members. The clamp comprises a first helical coil defining a cavity to receive a first rod member. The clamp further comprises a second helical coil defining a cavity to receive a second rod member. Finally, the clamp also comprises a connection and tightening device for constricting the first and second helical coils around the respective rod members. This embodiment may also be used as a device for securing a bone. In such a case, this embodiment may comprise a first and second stabilization bar, a pin, a pin attachment device, and a clamp. The pin has a first end suitable for insertion into a bone fragment, and a second end suitable for receiving the pin attachment device. The pin attachment device is suitable for receiving the pin and a stabilization bar. The clamp may be a clamp of the previously described embodiment comprising a first and second helical coil defining a cavity to receive the first and second stabilization bar, and a connection and tightening device for constricting the first and second helical coils around the respective stabilization bars.

In another embodiment of the present invention, a clamp for holding rod members may comprise a first and second connector, a first and second helical spring, and a connection and tightening device. The first and second connectors house the first and second helical springs, and the first and second helical springs define a cavity to house a rod member. The connection and tightening device secures and tightens the first and second connectors by causing the helical springs to constrict about the rod member. Also disclosed in the present invention is a device for securing a bone comprising this embodiment. The device comprises an above-described embodiment of the clamp of the present invention, and further includes a first and second stabilization bar, a pin and a pin attachment device. The pin has a first end suitable for insertion into a bone fragment and a second end suitable for securely receiving the pin attachment device. The pin attachment device is suitable for securely receiving the pin and the stabilization bar. As stated above, this device includes the clamp of this embodiment, wherein the first and second connectors house the first and second helical springs, and the first and second helical springs define cavities to house the first and second stabilization bar. The connection and tightening device secures and tightens the first and second connectors by constricting the helical springs about the stabilization bars.

In another embodiment of the present invention, a clamp for holding a rod member is disclosed, wherein the clamp comprises a helical coil that has a first loop, a second loop, and defines a cavity to receive a rod member. The loops may be formed from the ends of the coils or springs. This embodiment further includes a connection and tightening device received by the first and second loop for constricting the helical coil around a rod member. This embodiment is useful for removably attaching a rod to another device such as a stationary device, not necessarily another rod member.

Finally, in another embodiment of the present invention, a clamp for holding a rod member is disclosed, wherein the clamp comprises a hinge connector, a helical spring, and a connection and tightening device. The hinge connector houses a helical spring and the helical spring defines a cavity to house a rod member. The connection and tightening device secures and tightens the connector by causing the helical spring to constrict about the rod member. This embodiment is also useful for removably attaching a rod member to a stationary device, not necessarily another rod member.

BRIEF DESCRIPTION OF THE DRAWINGS

In FIG. 3, a threaded nut is the connection and tightening device.

FIG. 8 shows a close-up view of a toothed washer used as a coupling device in FIG. 5.

DETAILED DESCRIPTION OF THE PRESENT INVENTION

Figure 1:
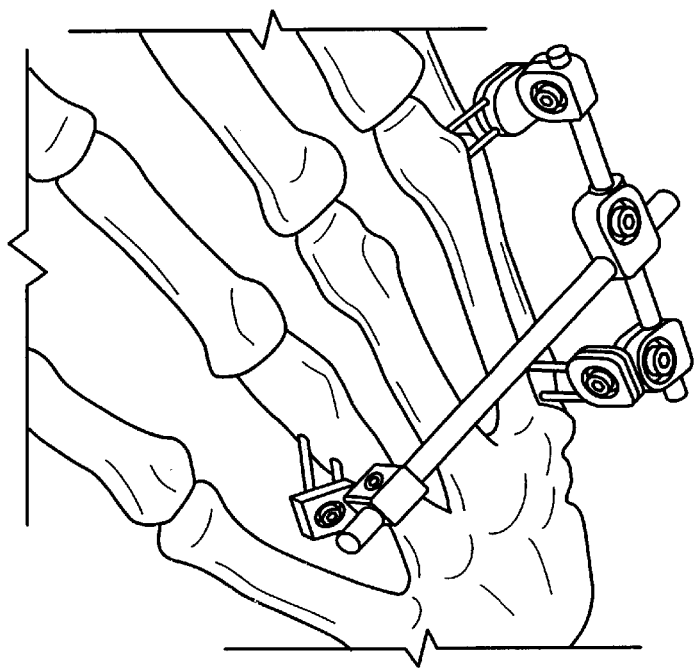
FIG. 1 shows a prior art bone stabilization clamp.
Figure 2:
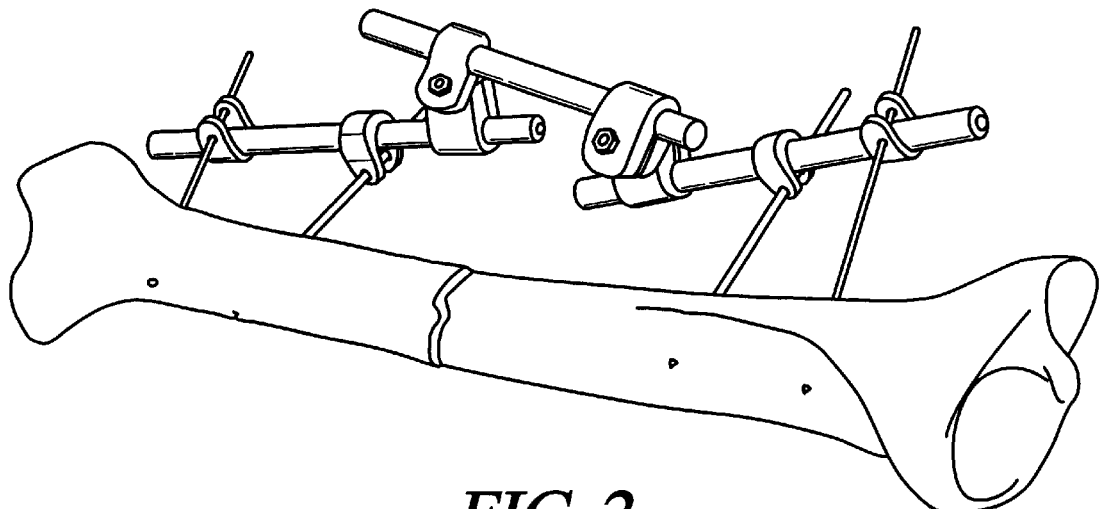
FIG. 2 shows a prior art bone stabilization clamp as described in U.S. Pat. No. 5,674,221.
Figure 3:
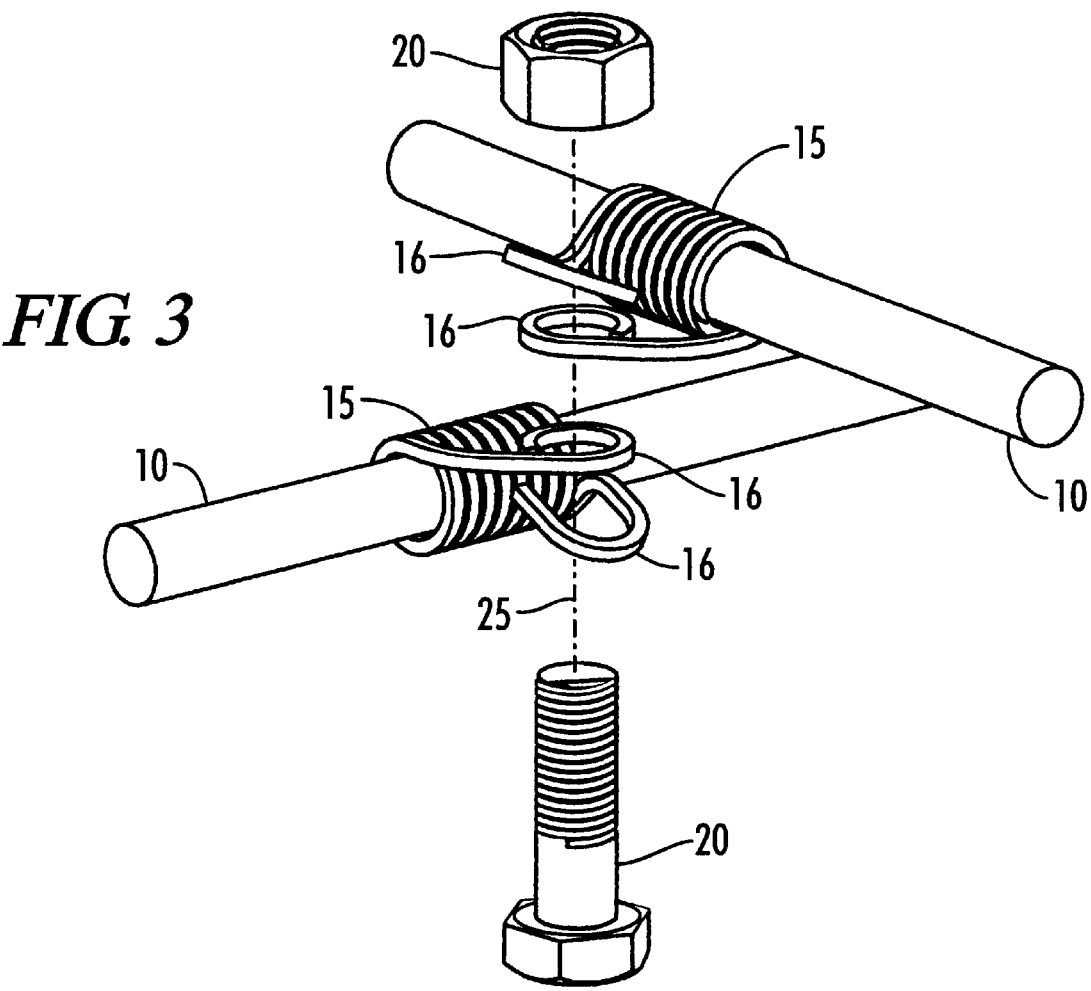
FIG. 3 shows a clamp of the present invention with a first and second helical coil.

As stated above, an embodiment of the present invention includes a clamp for holding rod members. The clamp comprises a first helical spring or coil and a second helical spring or coil. The helical springs 15 define a cavity to receive a rod member 10. The clamp further comprises a connection and tightening device 20 for constricting the first and second helical coils or springs 15 around the respective rod members 10. The helical springs 15 hold a rod 10 within their cavity or helix. The connection and tightening device 20 constricts the first and second helical coils around the respective rod members. In the embodiment shown in FIG. 3 the helical coils have a first end and second end that form loops 16 about a longitudinal axis 25. In another embodiment, the loops are simply securely attached to the spring. The connection and tightening device is received by the loops along the longitudinal axis 25. Then the connection and tightening device constricts the helical springs by constricting the distance between the first and second loop of each spring. Preferably, and as shown in FIG. 3, the connection and tightening device is a threaded bolt. In such a case, the loops then receive a bolt. However, the nature of the bolt is not known to be critical and therefore, may be a typical bolt as shown in FIG. 3 or, may be a bolt such as a single sex bolt that does not require tools to tighten. As stated above, when the bolt is tightened, the helical springs 15 are compressed and therefore securely grab the rod 10. Thus, the first and second helical coils or springs constrict the cavity around the rod members when constricted or acted upon by the connection and tightening device.

Figure 4:
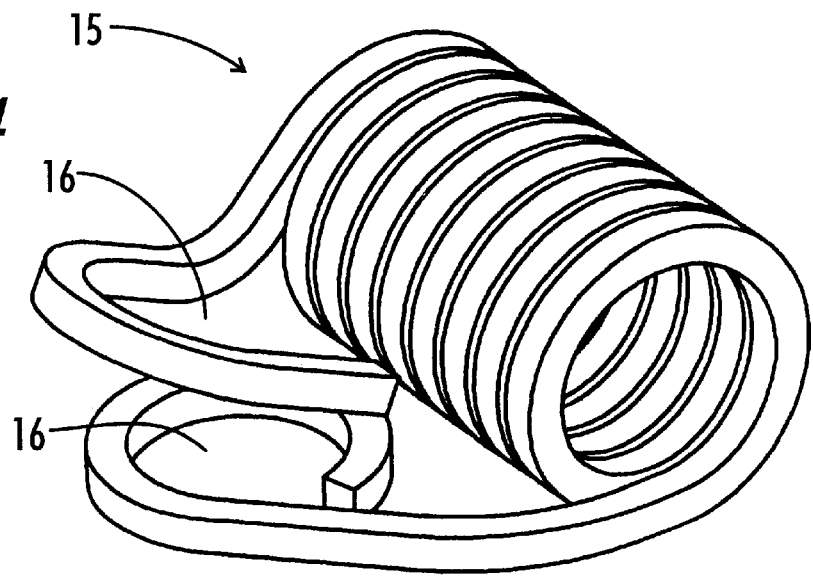
FIG. 4 shows a close-up view of a helical coil or spring used in the clamp of FIG. 3.

Preferably, the rod members are cylindrical, but each embodiment of the present invention may have applicability to other shapes. Also, FIG. 4 depicts spring 15 which may be used in respect to this embodiment of the present invention. In FIG. 4 the spring depicted is a square wire helical spring with a loop 16 on each end to receive the connection and tightening device, which, in turn, constricts the spring by constriction or pushing the loops together.

As stated above, the commercial applications of this invention are very broad and not limited to medical devices. However, this embodiment may be suitable for a medical device for securing a bone. Such a device includes a first and second stabilization bar, a pin, and a pin attachment device. The pin has a first end suitable for insertion into a bone fragment and second end for receiving a pin attachment device. The pin attachment device is suitable for receiving the pin and stabilization bar.

This embodiment also includes the clamp previously described, having a first helical coil defining a cavity to receive a first stabilization bar, a second helical coil defining a cavity to receive a second stabilization bar, and a connection and tightening device for constricting the first and second helical coil around the respective stabilization bars. Typically, the pin attachment devices releasably secures the pin with a stabilization bar.

Figure 5:
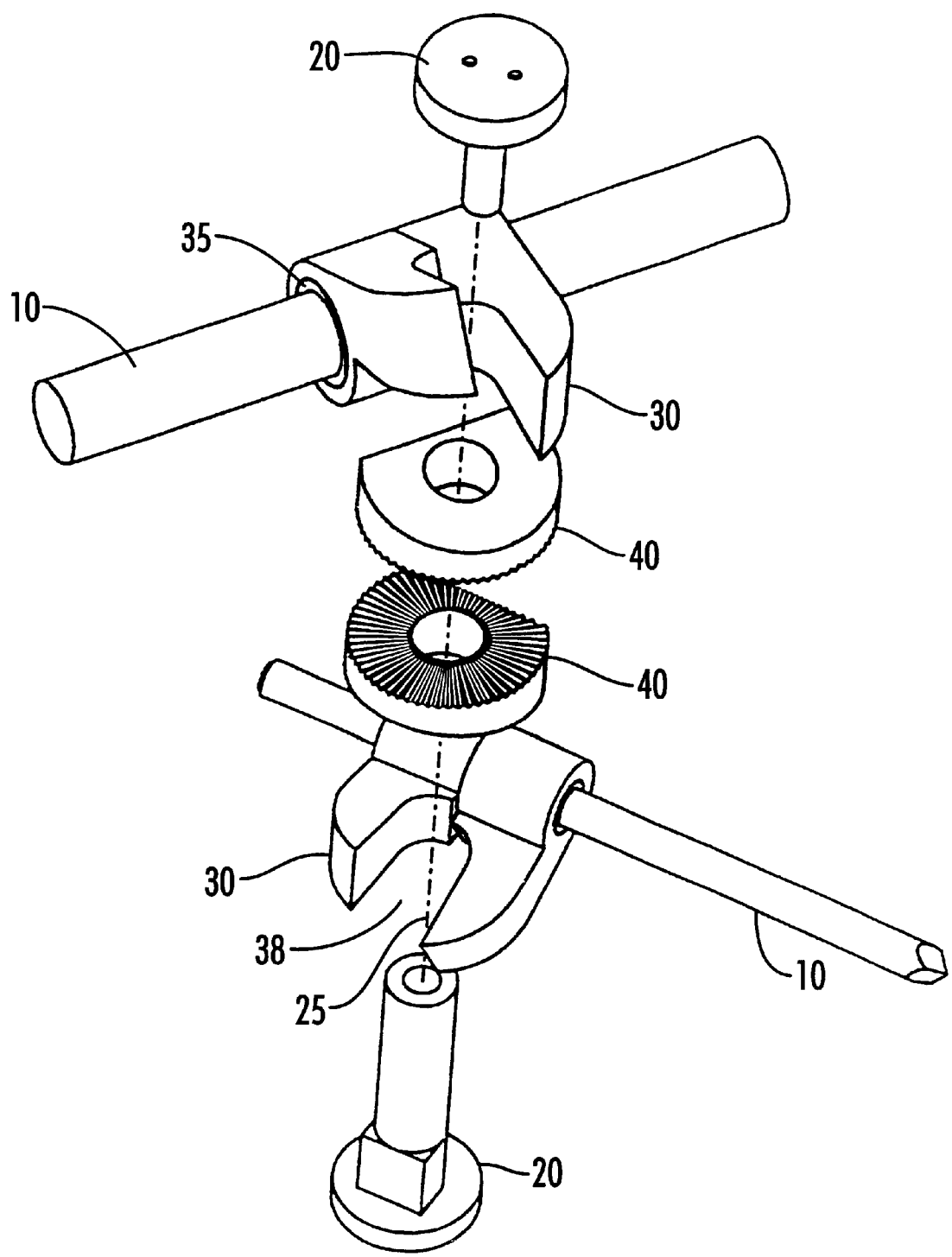
FIG. 5 shows a clamp of the present invention using a first and second connector, first and second helical springs, and a connection and tightening device. In the embodiment shown in FIG. 5, the clamp further comprises a pair of toothed washers as coupling devices.

Another embodiment of the present invention is a clamp for holding rod members as depicted in FIG. 5. This clamp comprises a first connector 30 and a second connector 30. The connectors have a helical coil or spring 35 housed within the connector. Additionally, a connection and tightening device 20 secures and tightens the first and second connectors 30 causing the helical springs within the connector to constrict about the rod members 10. With respect to this clamp, it is preferable that the rod members are round, but that feature is not required.

With this embodiment, the first and second connectors 30 may be hinge connectors. That is, the connectors 30 use a hinging action to constrict the helical spring. Additionally, the hinge connectors form a hinge cavity 38 about a longitudinal axis 25 to receive the connection and tightening device 20. Preferably, it is U-shaped to permit a free hinging action around the connection and tightening device 20. The helical springs may be housed within a bore 31 through the first and second connectors 30.

The clamp of this embodiment further comprises a coupling device 40 to secure the first and second connectors one to the other. In a preferred embodiment, the coupling devices are corresponding toothed washers.

As stated above, the connection and tightening device 20 may be a bolt. In this embodiment the bolt passes through the hinge cavity along a longitudinal axis to secure the connection devices. The bolt may be a sex bolt that does not require tools to tighten. When the bolt is in a tightened state, pressure is applied on the hinge which in turn through the positioning pins applies pressure on the spring and the spring constricts around the rod members.

Figure 6:
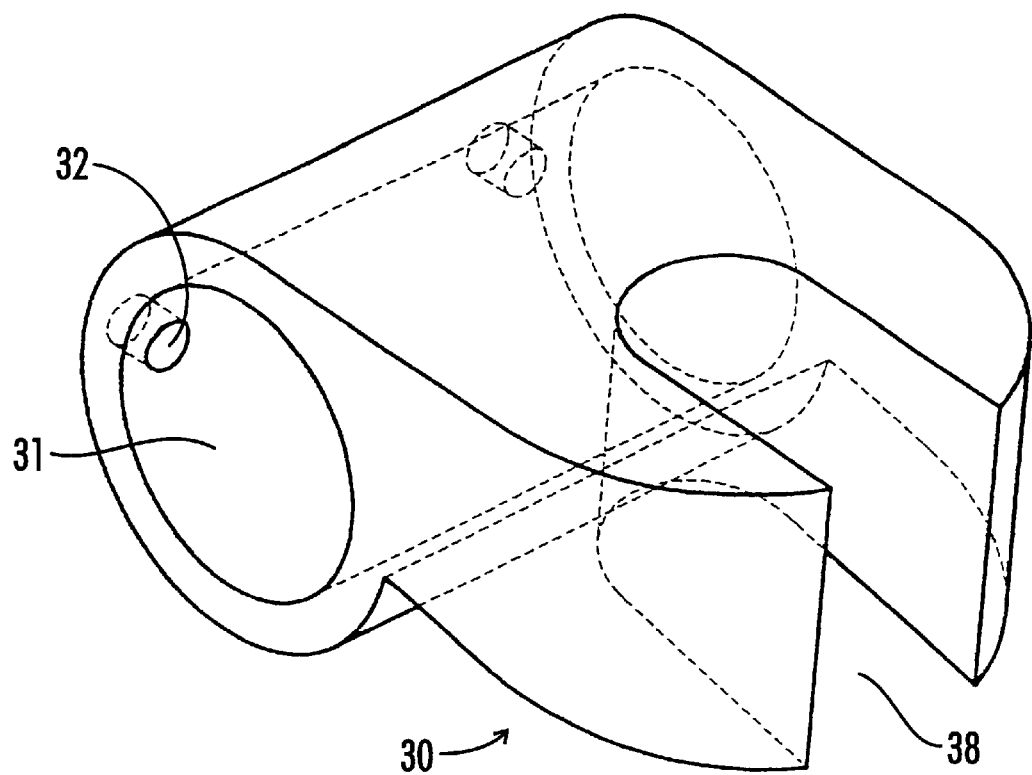
FIG. 6 shows a close-up view of a hinged connector in the embodiment shown in FIG. 5. The hinged connector of FIG. 6 is shown prior to the hinge being cut.

FIG. 6 is a view of a hinge connector before the hinge connector is cut to permit the hinging action. A bore 31 is cut through the connector to house the helical spring, which is inserted into the bore of the connector 31. The connector further comprises positioning holes 32 which correspond with positioning holes found on the spring. When the spring is inserted into the bore, it may be held in place by inserting a positioning pin to be received by the helical spring positioning hole and a bore positioning hole. The hinge cavity 38 is shown, which receives the connection and tightening device.

Figure 7:
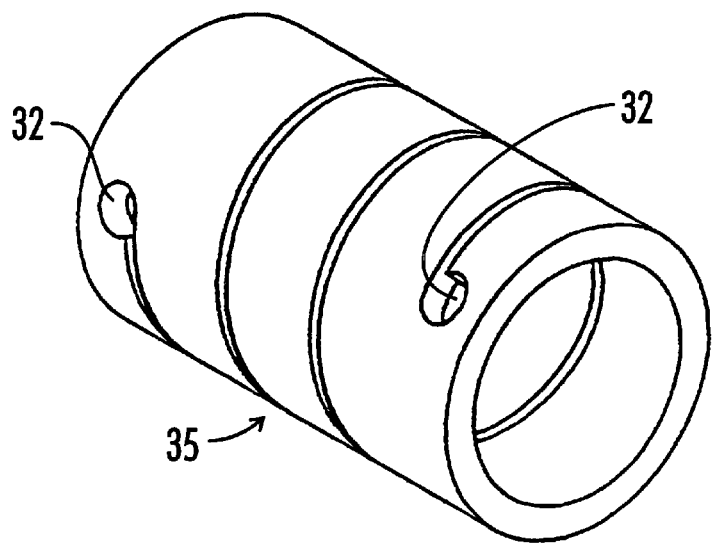
FIG. 7 shows a helical spring or coil suitable for use in the embodiment shown in FIG. 5.

FIG. 7 shows a spring 35 of this embodiment. The position holes 32 are shown.

A preferred embodiment of the coupling device 40 of the present invention is toothed with a star pattern, as depicted in FIG. 8. The coupling device as shown in FIG. 8 is shaped somewhat oblong to prevent rotation so that the coupling device may be tightened from the opposite end without gripping the oblong end.

Figure 9:
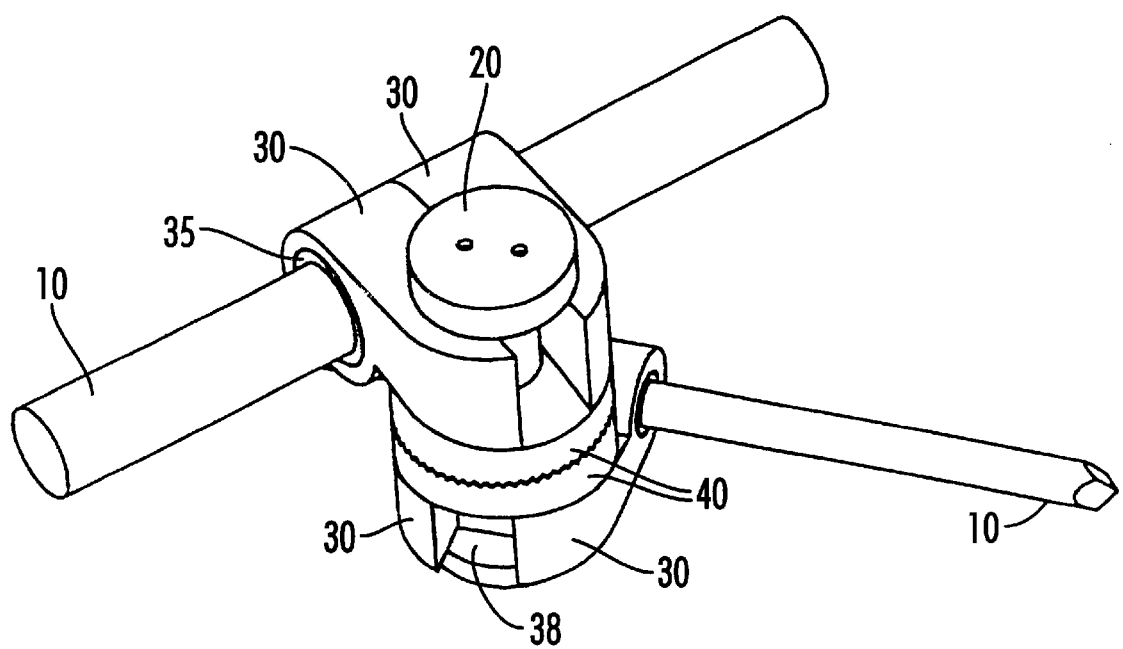
FIG. 9 shows the embodiment of FIG. 5 in a fully clamped position.

FIG. 9 shows a clamp of this embodiment in a compressed and tightened state whereby the hinge connectors are securely holding the rods.

Figure 10:
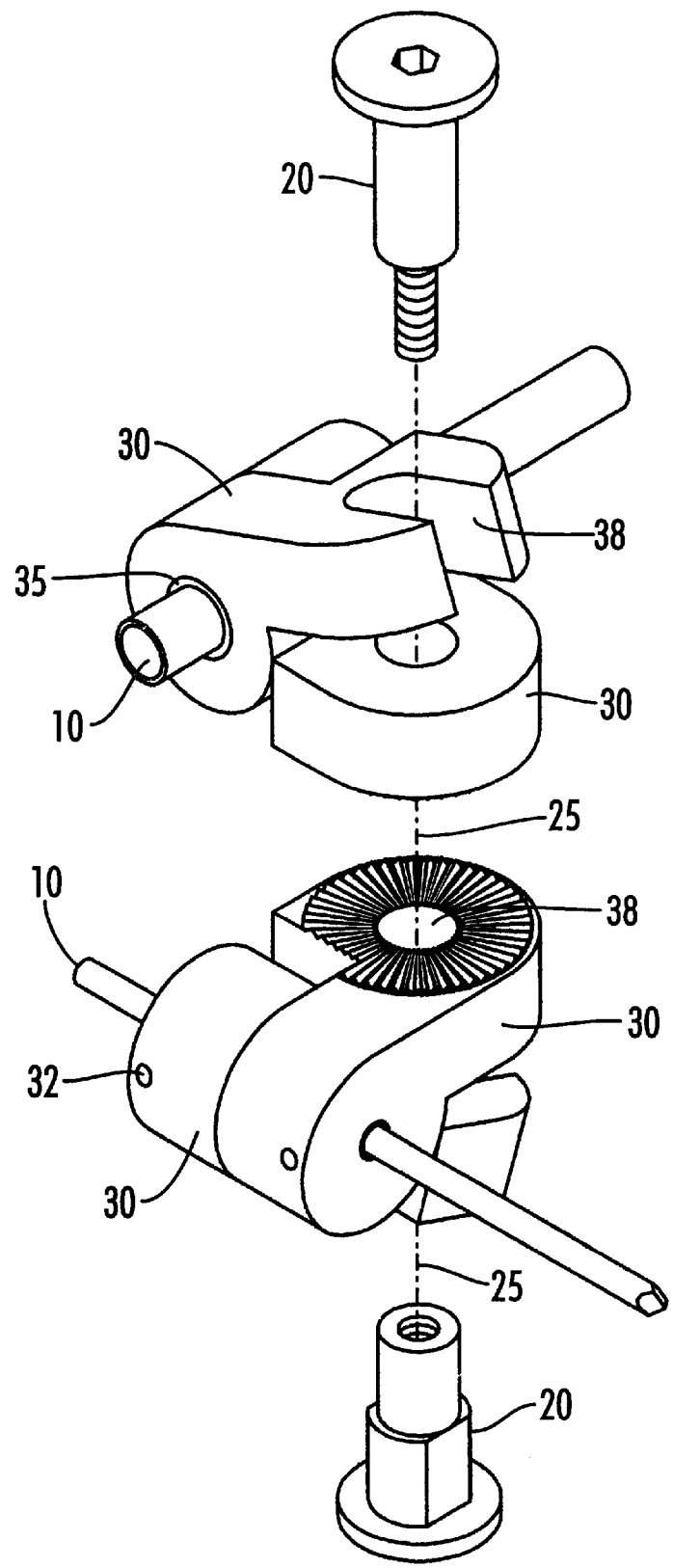
FIG. 10 shows an embodiment of the present invention wherein the hinge connectors are J-shaped and comprise a toothed surface arranged so that the toothed surface of the first J-shaped hinge connector securely engages the toothed surface of the second J-shaped hinge connector.
Figure 11:
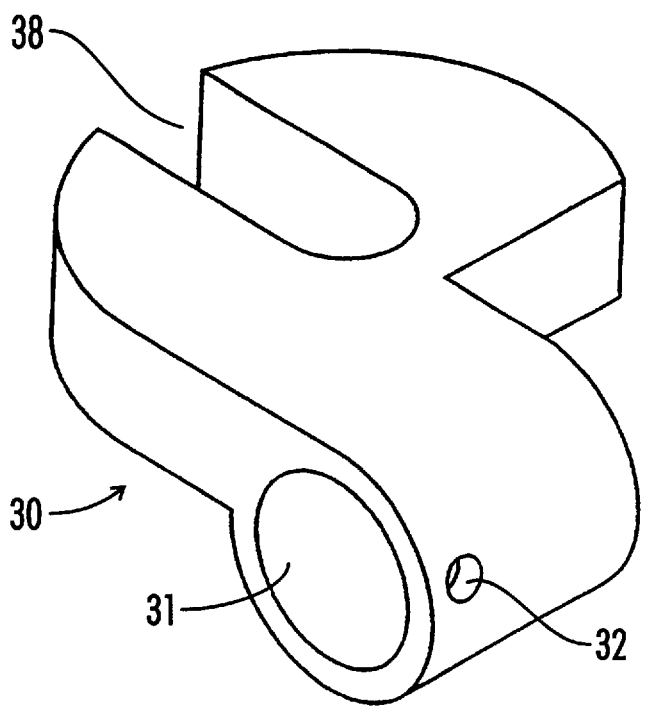
FIG. 11 shows a close-up view of a J-shaped-hinged connector.
Figure 12:
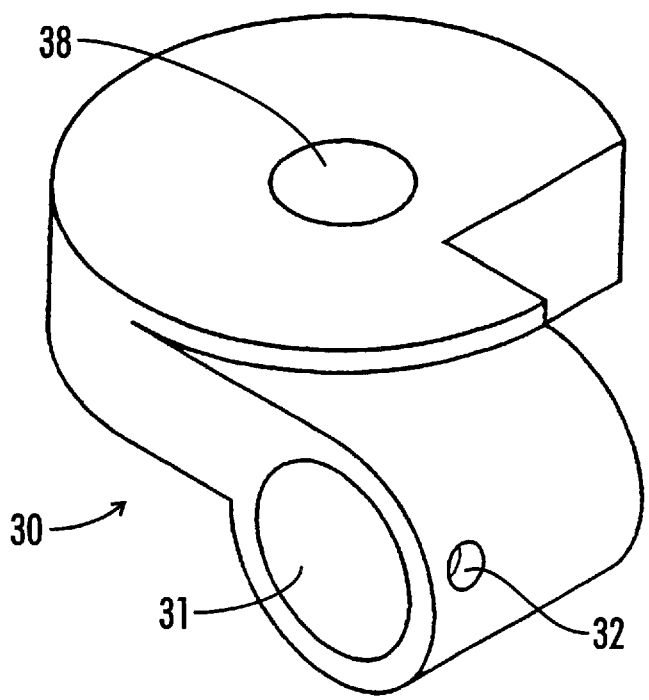
FIG. 12 shows a J-shaped hinged connector.
Figure 13:
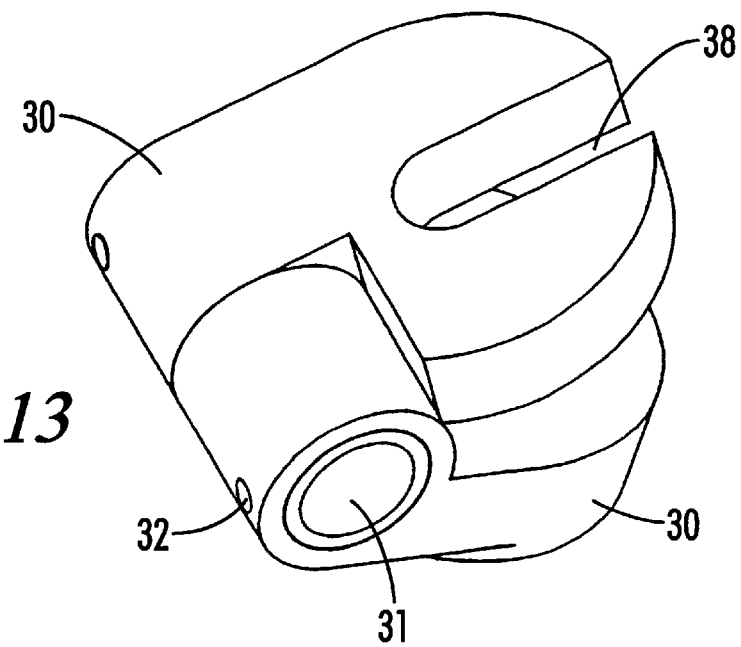
FIG. 13 shows a view of two J-shaped hinge connectors oriented such that the connection device can be received by the hinge cavity.

In another embodiment of the present invention, the first and second hinge connectors 30 may have a toothed surface arranged so that the toothed surface of the first hinge connector securely engages the toothed surface of the second hinge connector. This embodiment is shown in FIG. 10. Furthermore, the first and second hinge connectors 30 may be J-shaped hinges as shown in FIG. 10. Preferably, the J-shaped hinges have a hinge cavity 38 that is an open cavity connector as shown in FIG. 17 opposed by a closed hinge cavity connector as shown in FIG. 12. The open hinge connector cavity is formed to allow full unobstructed hinging action. The hinges of this embodiment as shown in FIGS. 11 and 12 also include a bore hole 31 for receiving a spring and a positioning hole 32. The open cavity hinge and the closed cavity hinge may be placed together as shown in FIG. 13. As can be seen in FIG. 13, it is preferable to have one open hinge cavity, because the open cavity allows for full hinging action when tightened without interference from the connection and tightening device.

Figure 14:
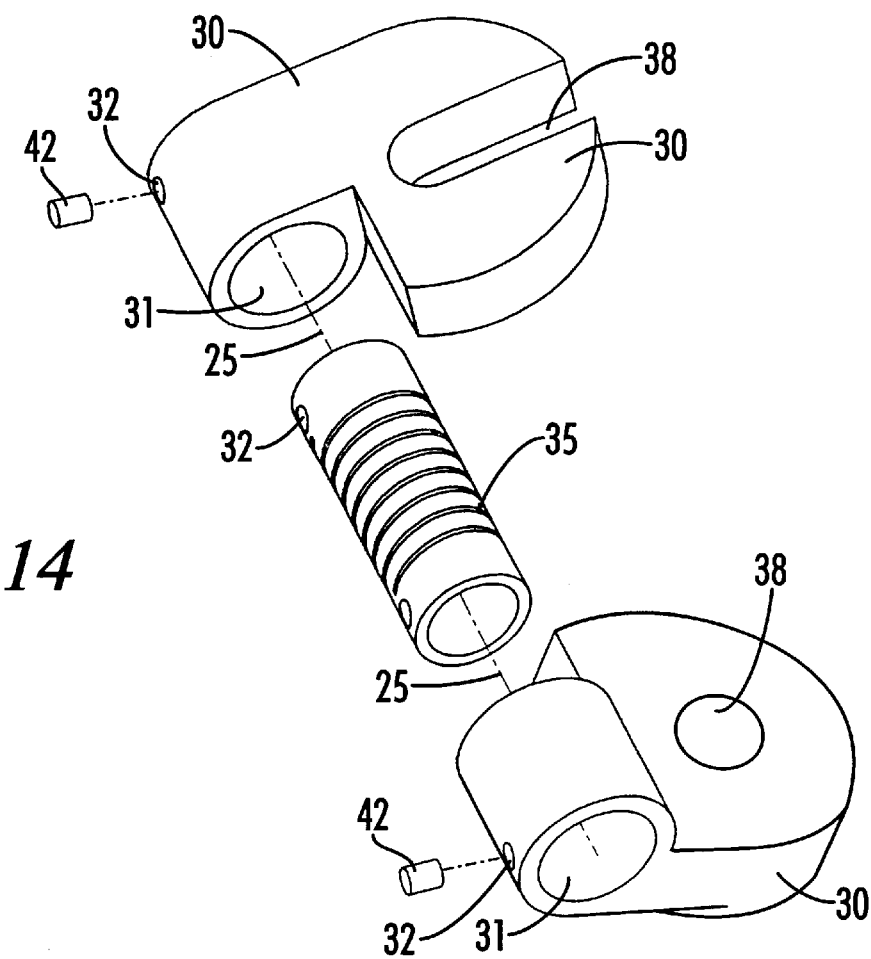
FIG. 14 shows an exploded view of the embodiment shown in FIG. 13.

FIG. 14 shows an exploded view of the embodiment of FIG. 10, with an open cavity J-shaped hinge being paired with a closed cavity J-shaped hinge. The spring 35 is inserted into each respective bore hole 31. The positioning holes 32 are aligned and the positioning pin 42 is inserted into the positioning holes 32 of the connector 30 and the spring 35. The hinge should be positioned such that it is open when a rod is inserted through the cavity or helix of the spring 35. Therefore, when the connection and tightening device (not shown in FIG. 14) is applied through the hinge cavity 38, the hinges are closed and therefore pressure is exerted on to the spring which constricts on to the rod.

Figure 15:
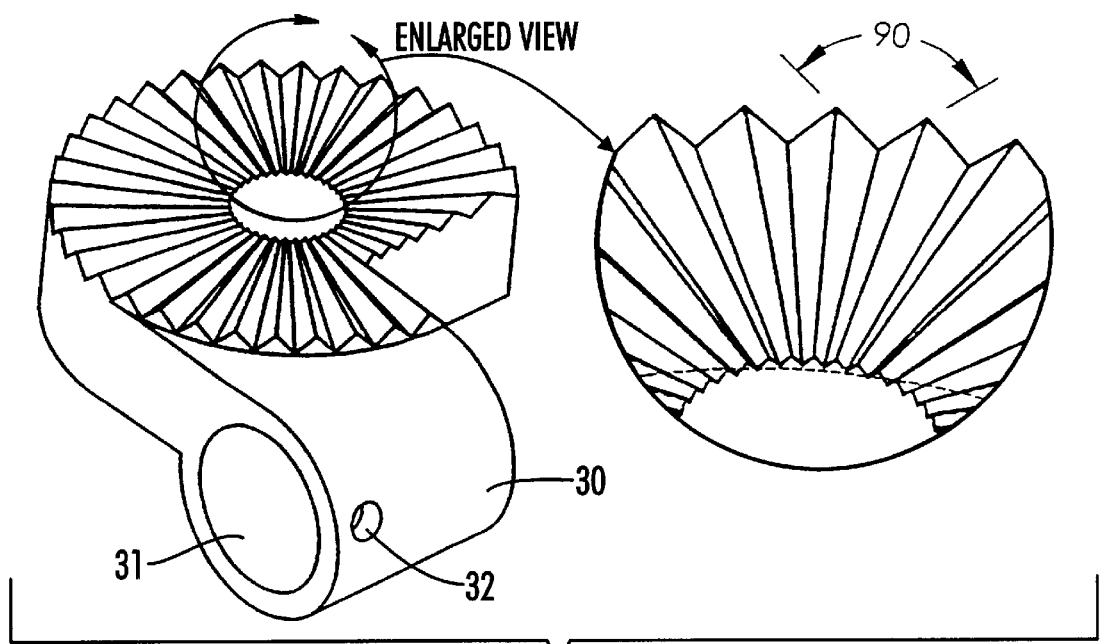
FIG. 15 shows a close-up view of the embodiment where a connector is a J-shaped connector and further comprises a toothed surface.

FIG. 15 shows an embodiment of the present invention where the hinge connectors 30 have a toothed surface arranged so that the toothed surface of the first hinge connector may securely engage the toothed surface of the second connector. The bore hole 31 and positioning hole 32 are shown. A preferred toothed surface is the star shaped pattern shown in FIG. 15. The star shaped pattern is excellent in preventing slippage between the connectors.

Figure 16:
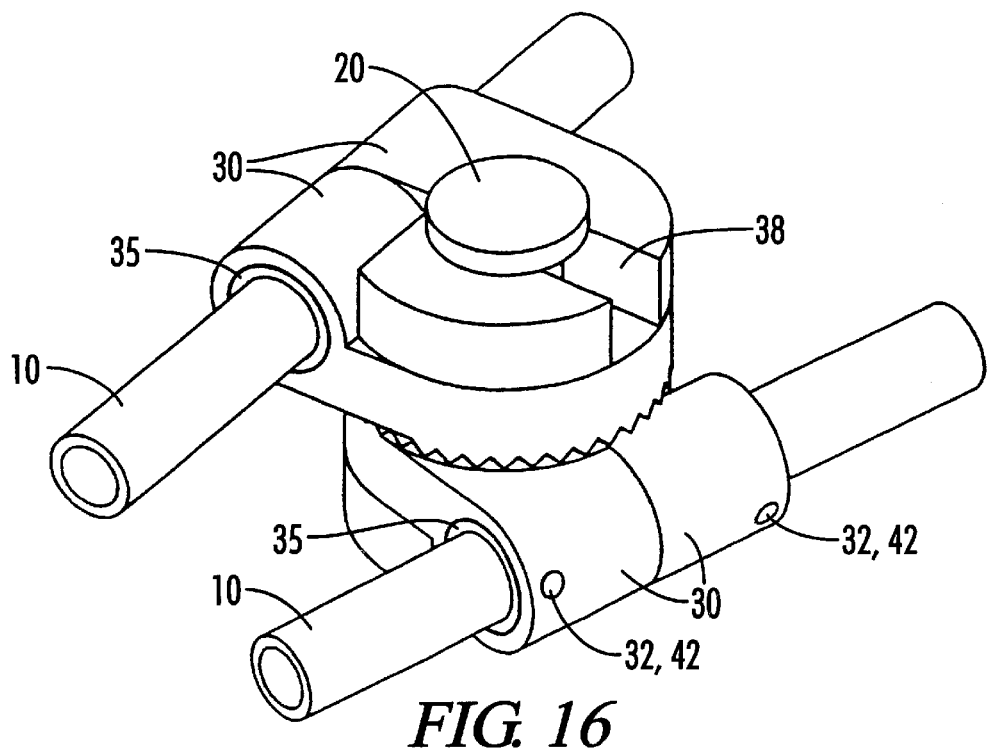
FIG. 16 shows a clamp of the present invention wherein the J-shaped connectors have toothed surfaces and the clamp is in the fully clamped position.

FIG. 16 shows a clamp of FIG. 10 in a fully tightened and compressed position.

When the J-shaped connectors do not contain a toothed surface to act as a coupling device, they may have a separate coupling device used in a manner that prevents slippage between the connection devices.

The clamp of this and the above embodiments may also be used for removably attaching a rod to another device, not necessarily another rod member. In this embodiment, only one connector with a helical spring is required.

As with the clamp described above, this clamp may also be used as a device for securing a bone. In such a case, the device will further comprise a first and second stabilization bar, a pin, and a pin attachment device. The pin must have a first end suitable for insertion into a bone fragment and a second end suitable for securely receiving the pin attachment device. The pin attachment device is suitable for securely receiving the pin and the stabilization bar. Finally, the clamp may be the clamp previously described.

All patents and other publications disclosed or discussed above are herein expressly incorporated by reference.

This invention thus being described, it would be obvious that the same be varied in many ways. Such variations are not to be regarded as a departure from the spirit and scope of the present invention, and all such modifications as would be obvious to one of ordinary skill in the art are intended to be included within the scope of this invention.

I claim:

1. A clamp for holding rod members, comprising:
   a first helical coil defining a cavity to receive a first rod member;
   a second helical coil defining a cavity to receive a second rod member; and
   a connection and tightening device for constricting the first and second helical coils around the respective rod members.

2. The clamp of claim 1, further comprising:
   a longitudinal axis; and wherein:
      the first helical coil has first a loop about the longitudinal axis and a second loop about the longitudinal axis; and
      the second helical coil has a first loop about the longitudinal axis and a second loop about the longitudinal axis; and
      the connection and tightening device is received by the loops of the first and second helical coils.

3. The clamp of claim 1, wherein:
   the connection and tightening device is a threaded bolt.

4. The clamp of claim 1, wherein:
   the first and second helical coils act as springs to constrict the cavity around the rod members when constricted by the connection and tightening device.

5. The clamp of claim 1, wherein:
   the rod members are cylindrical.

6. The clamp of claim 1, wherein:
   the first and second helical coils are square wire.

7. The clamp of claim 6, wherein:
   the first helical coil has a first end forming the first loop about the longitudinal axis and a second end forming the second loop about the longitudinal axis; and
   the second helical coil has a first end forming the first loop about the longitudinal axis and a second end forming the second loop about the longitudinal axis.

8. A device for securing a bone, comprising:
   a first and second stabilization bar;
   a pin;
   a pin attachment device;
   with the pin having a first end suitable for insertion into a bone fragment, and a second end suitable for receiving the pin attachment device, and the pin attachment device being suitable for receiving the pin and the first or second stabilization bar; and
   a clamp, having:
      a first helical coil defining a cavity to receive the first stabilization bar;
      a second helical coil defining a cavity to receive the second stabilization bar; and
      a connection and tightening device for constricting the first and second helical coils around the respective stabilization bars.

9. The device of claim 8, wherein the pin attachment device releasably secures the pin with the stabilization bar.

10. The device of claim 8, further comprising:
    a longitudinal axis; and wherein
    the first helical coil has a first end forming a loop about the longitudinal axis and a second end forming a loop about a longitudinal axis; and
    the second helical coil has a first end forming a loop about a longitudinal axis and a second end forming a loop about a longitudinal axis;
    and the connection and tightening device is received by the loops of the first and second helical bolts.

11. The device of claim 8, wherein the first and second helical coils are square wire.

12. The device of claim 8, wherein the connection and tightening device is a threaded bolt.

13. The device of claim 12, wherein the bolt is a single sex bolt.

14. A clamp for holding rod members, comprising:
    a first connector,
    a second connector,
    a first helical spring,
    a second helical spring, and
    a connection and tightening device; wherein
       the first connector houses the first helical spring, and the first helical spring defines a cavity to house a first rod member;
       the second connector houses the second helical spring, and the second helical spring defines a cavity to house a second rod member; and
       the connection and tightening device secures and tightens the first and second connectors by causing the helical springs to constrict about the rod members.

15. The clamp of claim 14, wherein:
    the first and second connectors are hinge connectors.

16. The clamp of claim 15, further comprising:
    a longitudinal axis; and
    wherein the hinge connectors form a hinge cavity about the longitudinal axis to receive the connection and tightening device.

17. The clamp of claim 14, wherein the first and second connectors comprise a bore to house the helical spring.

18. The clamp of claim 17, wherein the helical spring further comprises a positioning hole, and the bore further comprises a positioning hole, and the clamp further comprises:
    a positioning pin to be received by the helical spring positioning hole and the bore positioning hole and to secure the spring within the bore.

19. The clamp of claim 14, further comprising a coupling device to secure the first and second connector.

20. The clamp of claim 19, wherein the coupling device is two corresponding toothed washers.

21. The clamp of claim 14, wherein the connection and tightening device is a bolt.

22. The clamp of claim 21, wherein the connection and tightening device is a single sex bolt.

23. The clamp of claim 15, wherein the first and second hinge connectors have a toothed surface arranged so that the toothed surface of the first hinge connector securely engages the toothed surface of the second connector.

24. The clamp of claim 23, wherein the first and second hinge connectors are J-shaped hinges.

25. The clamp of claim 14, wherein the helical springs are machined springs.

26. The claim of claim 15, wherein the hinge connectors are J-shaped hinge and the clamp further comprises:
a coupling device to secure the first and second connector.

27. A device for securing a bone, comprising:
a first and second stabilization bar;
a pin;
a pin attachment device; wherein
the pin has a first end suitable for insertion into a bone fragment, and a second end suitable for securely receiving the pin attachment device, and the pin attachment device is suitable for securely receiving the pin and a stabilization bar; and
a clamp, the clamp including:
a first and second rod member;
a first and second connector;
a first and second helical spring; and
a connection and tightening device; wherein:
the first connector houses the first helical spring, the first helical spring defining a cavity to house the first stabilization bar;
the second connector houses the second helical spring, the second helical spring defining a cavity to house the second stabilization bar; and
the connection and tightening device secures and tightens the first and second connectors by constricting the helical springs about the stabilization bars.

28. The device of claim 27, wherein the first and second connectors are hinge connectors.

29. The device of claim 28, further comprising:
a longitudinal axis; and
wherein the hinge connectors form a hinge cavity about the longitudinal axis to receive the connection and tightening device.

30. The device of claim 29, wherein the first and second connectors comprise a bore to house the helical spring.

31. The device of claim 30, wherein the helical springs further comprise a positioning hole, and the bore further comprises a positioning hole, and the clamp further comprises:
a positioning pin to be received by the helical spring positioning hole and the bore positioning hole to secure the helical spring within the bore.

32. The device of claim 31, wherein the clamp further comprises a coupling device to secure the first and second connector.

33. The device of claim 32, wherein the coupling device is two corresponding toothed washers.

34. The device of claim 28, wherein the first and second hinge connectors have a toothed surface arranged to that the toothed surface of the first hinged connector securely engages the toothed surface of the second connector.

35. The device of claim 29, wherein the hinge connectors are J-shaped.

36. A clamp for holding a rod member, comprising:
a hinge connector;
a helical spring; and
a connection and tightening device; wherein
the hinge connector houses the helical spring, and the helical spring defines a cavity to house a rod member; and
the connection and tightening device secures and tightens the connector by causing the helical spring to constrict about the rod member.

37. The clamp of claim 36, wherein the hinge connector forms a hinge cavity to receive the connection and tightening device.

38. The clamp of claim 36, wherein the hinge connector comprise a bore to house the helical spring; and wherein:
the helical spring further comprises a positioning hole, and the bore further comprises a positioning hole, and the clamp further comprises:
a positioning pin to be received by the helical spring positioning hole and the bore positioning hole and to secure the spring within the bore.

39. The clamp of claim 37, wherein the first and second hinge connectors are J-shaped hinges.

* * * * *